United States Patent [19]

Nelson et al.

[11] 4,345,028

[45] Aug. 17, 1982

[54] BACTERIA GROWING DEVICE

[75] Inventors: Robert L. Nelson, Minneapolis; Michael W. Downing, White Bear Lake, both of Minn.

[73] Assignee: Minnesota Mining and Manufacturing Company, St. Paul, Minn.

[21] Appl. No.: 193,933

[22] Filed: Oct. 6, 1980

Related U.S. Application Data

[63] Continuation of Ser. No. 5,149, Jan. 22, 1979, Pat. No. 4,252,904, which is a continuation-in-part of Ser. No. 808,459, Jun. 21, 1977, abandoned.

[51] Int. Cl.³ .......................................... C12Q 1/24
[52] U.S. Cl. ............................ 435/30; 435/292; 435/294; 435/299; 435/810
[58] Field of Search .............. 435/29, 30, 34, 292, 435/294, 295, 296, 299, 243, 253, 260, 802, 810; 73/425, 425.4 P; 128/638, 743, 759; 206/205, 207; 215/100 R; 422/100; 30/168, 278, 280, 314, 315, 358; 145/24

[56] References Cited

U.S. PATENT DOCUMENTS

| 368,344 | 8/1887 | Layer | 73/425 |
|---|---|---|---|
| 376,136 | 1/1888 | Burrows | 30/358 X |
| 544,475 | 8/1895 | Booth et al. | 30/278 X |
| 869,063 | 10/1907 | Cryer | 30/358 |
| 884,350 | 4/1908 | Carman | 30/358 |
| 1,041,049 | 10/1912 | Elliott | 30/280 |
| 2,176,626 | 10/1939 | Gentry | 30/168 X |
| 3,077,780 | 2/1963 | Takatsy | 422/100 X |
| 3,176,396 | 4/1965 | Straka | 30/168 |
| 3,252,331 | 5/1966 | Lancaster | 73/425.4 P |
| 3,433,712 | 3/1969 | Gerarde | 435/30 X |
| 3,479,881 | 11/1969 | Unger | 73/425.4 P |
| 3,902,972 | 9/1975 | Beckford | 435/30 X |
| 3,912,596 | 10/1975 | Hague et al. | 435/30 X |
| 4,252,904 | 2/1981 | Nelson et al. | 435/30 X |

FOREIGN PATENT DOCUMENTS 1234044  6/1971  United Kingdom .

Primary Examiner—Robert J. Warden
Attorney, Agent, or Firm—Cruzan Alexander; Donald M. Sell; Jennie G. Boeder

[57] ABSTRACT

This invention relates to a device for growing bacteria from an initial population to a final predetermined population, said device including a medium for such growth and a means for obtaining a predetermined population for inoculation of said medium.

7 Claims, 9 Drawing Figures

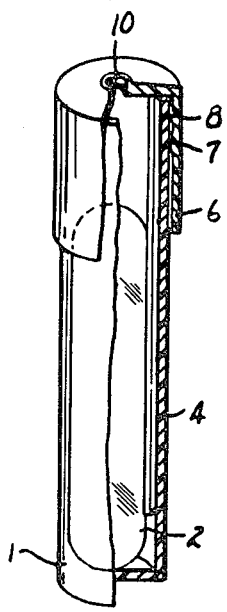
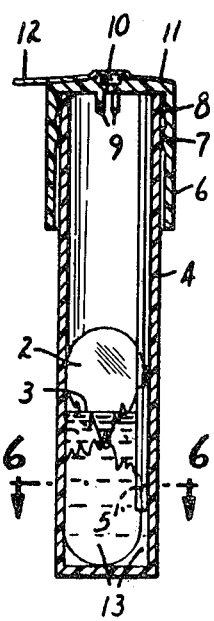
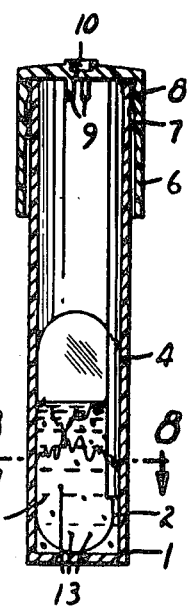
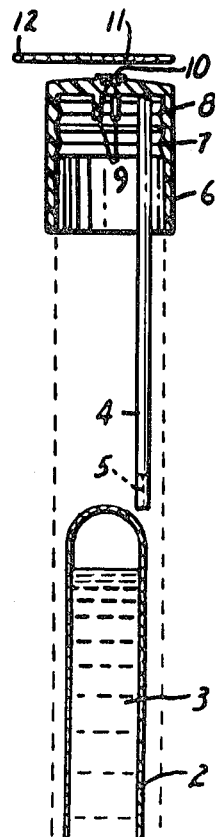
FIG. 2  FIG. 5  FIG. 7
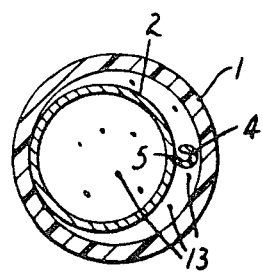
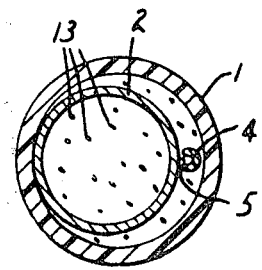
FIG. 6  FIG. 8
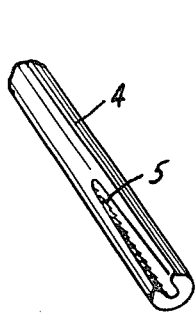
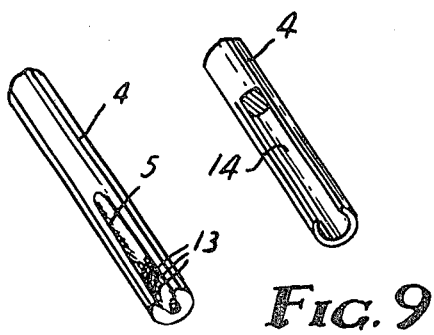
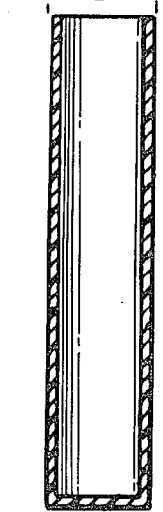
FIG. 3  FIG. 4  FIG. 9  FIG. 1

BACTERIA GROWING DEVICE

This application is a continuation of copending application Ser. No. 5,149, filed Jan. 22, 1979, issued as U.S. Pat. No. 4,252,904 on Feb. 24, 1981 which is a continuation-in-part of application Ser. No. 808,459, filed June 21, 1977, now abandoned.

This invention relates to a device for growing bacteria. Specifically, this invention relates to a device for growing bacteria from an initial population to a final predetermined population, said device including a medium for such growth and a means for obtaining a predetermined population for inoculation of said medium.

In a patent application filed concurrently with this application growth limiting media are described and claimed. These media are described as being useful in a number of procedures utilized to identify the bacteria or to determine the susceptibility of the bacteria to certain antibiotics. In such procedures it is necessary to have the bacteria at the beginning of the test procedure in a certain concentration range (colony forming units per milliliter (CFU/ml)) or the final result will not be accurate. For example, in an article entitled "Antibiotics Susceptibility Testing by Standardized Single-Disc Method", *The American Journal of Clinical Pathology*, Vol. 45, No. 4, April, 1966, Pages 293–296 and in the "Performance Standards for Antimicrobial Disc Susceptibility Test", ASM-2, promulgated by the National Committee for Clinical Laboratory Standards, the Kirby-Bauer procedure for determining the susceptibility of rapidly growing bacteria to antibiotics and chemotherapy agents is described.

The Kirby-Bauer procedure normally involves growing on an agar plate colonies of bacteria obtained from a patient. A wire loop is used to pick from 4 to 5 colonies of the bacteria and introduce them into test tubes containing 4 to 5 milliliters of soybean casein digest broth. The tubes are then incubated for 2 to 8 hours to produce a bacterial suspension of moderate cloudiness. The suspension is then diluted, if necessary, with saline solution or like broth to a density visually equivalent of that of a standard prepared by adding 0.5 milliliters of 1% $BaCl_2$ to 99.5 milliliters of 1% $H_2SO_4$ (0.36 N) (0.5 McFarland standard hereinafter the McFarland standard). A plate containing Mueller-Hinton agar is then streaked with the bacterial broth suspension using a cotton swab. After the inoculum has dried, a paper disc containing an antibiotic or chemotherapeutic agent is applied to the agar. The plates are incubated. After overnight incubation the area around each disc wherein there is an absence of bacteria growth is measured. This is known as the zone of inhibition and is used to determine which antibiotic will be useful in combating the particular bacteria.

In order for the Kirby-Bauer technique to be accurate there must be approximately $1 \times 10^8$ CFU/mc included in the medium which is streaked onto the agar plate. Usually the level of growth is determined by using the visual comparison with the McFarland standard described above. The time period to reach this concentration of bacteria may vary from 2 to 8 hours depending on the bacteria. If the bacteria are allowed to grow in excess of $1 \times 10^8$ CFU/milliliter and become more turbid than the McFarland standard the medium must be diluted in order to be equivalent to the standard.

Another method of determining the susceptibility of bacteria to various antibiotics is called the MIC or Minimum Inhibitory Concentration Test. This test is discussed in *Current Techniques for Antibiotics Susceptibility Testing*, Albert Balows, c 1974, pages 77–87. This method involves preparation of a series of concentrations of an antibiotic either in a liquid or solid medium which will support the groth of a bacteria to be tested. Liquid media are conveniently dispensed in test tubes and solid media are usually poured into petri dishes. It is common practice to prepare a range of antibiotic concentrations as a series of two-fold dilutions in order to carry out the test. Each tube or petri dish is inoculated with the bacteria in question. After a period of incubation the bacterial growth or absence of growth of each antibiotic concentration is observed. In this way the minimum inhibitory concentration of the antibiotic is determined to the nearest dilution when used in a series. This is the most accurate method of determining the inhibitory concentration. However, this method did not gain popularity until recently when the laborious effort of making the dilutions was simplified. The diluted antibiotic is inoculated in the MIC test with a bacteria when it is of certain concentration, i.e., normally $10^5$ to $10^6$ CFU/ml. Broth containing bacteria growth to the equivalent of the McFarland standard, i.e., approximately $1 \times 10^8$ CFU/ml is diluted to obtain this concentration.

The aforesaid susceptibility tests as well as other tests for determining the types of bacteria or susceptibility thereof to antibiotics require that a certain predetermined amount of bacteria be utilized in the test to inoculate the plates upon which the paper disc will be placed in the case of the Kirby-Bauer test or to inoculate the diluted antibiotics in the case of the MIC test. This is required in order for the test to be accurate. If a lesser concentration of bacteria is utilized in the test, the result would indicate that the bacteria is more suscepticle to the antibiotic than it would be as an actual fact. On the other hand, if the bacteria are present in a higher concentration, the test results would indicate that a higher concentration of the antibiotic would be required in order to inhibit the growth of the bacteria. Both indications would be erroneous.

In order for the aforesaid tests to be performed or tests similar thereto to be performed it is necessary for the laboratory technician to take a sample of bacteria from 4 or 5 colonies of bacteria from the agar plate upon which the bacteria has been growing and place it in a broth growing medium such as above described for 2 to 8 hours. The medium is checked periodically to determine whether or not a sufficient concentration of bacteria have grown to be equivalent to the McFarland standard. From a visual examination of the medium one will find that some medium cultures of bacteria have not grown to the proper concentration while others have grown beyond the appropriate concentration. The former requires that the technician allow the bacteria to grow longer whereas the latter requires a dilution to bring the concentration back to that of the standard. All of these measures are tedious and time consuming.

The application filed concurrently herewith described a growth limiting media which has been found which will grow bacteria to a certain predetermined concentration or population level. That medium is capable of growing at least one species from two different genera of aerobic, pathogenic, rapidly growing bacteria from a beginning population to a determined ending population at which said growth of said bacteria substantially subsides due to the lack of nutrient in the medium and wherein said bacteria remain viable for at least 18 hours; said medium comprising an aqueous solution comprising a carbon source, a nitrogen source, vitamins and minerals of sufficient quantity to provide said growth and in a form usuable by said bacteria for said growth.

The general description of that medium will be described herein for purposes of completeness.

The bacteria upon which the medium is useful are aerobic bacteria, i.e., those which use oxygen to grow. The bacteria are also pathogenic in that they cause diseases and are rapidly growing in that they have a generation time of 50 minutes or less.

The medium is useful with both gram-negative as well as gram-positive aerobic, pathogenic, rapidly growing bacteria. However, the type and amount of the various ingredients in the medium are normally different for the gram-positive than for the gram-negative and the time period required to obtain the requisite concentration for the gram-positive tends to be longer than that for the gram-negative bacteria.

The growth medium will grow at least one species from two different genera of aerobic, pathogenic bacteria. Normally the medium will grow at least one species from two genera of gram-positive bacteria or at least one species from at least two genera of gram-negative bacteria. Within gram-positive aerobic bacteria, there are two genera which include the bacteria that cause most diseases for which normal bacteria and susceptibility testing is performed. These are Staphylococcus and Streptococcus. If the medium will grow species from each of these two genera then it allows one to merely test the bacteria to determine whether it is gram-positive or negative using a gram stain test. If the bacteria is gram-positive the medium which grow the gram-positive bacteria is used and the medium will grow the bacteria to the level desired such as to the equivalent of the McFarland standard.

If the bacteria is determined to be gram-negative using the gram stain test, the bacteria could be from a much larger number of genera. Sixteen genera represent the bacteria found to be the cause of 99% of illnesses caused by gram-negative aerobic bacteria. These gram-negative genera include: Escherichia, Shigella, Edwardsiella, Salmonella, Arizona, Citrobacter, Klebsiella, Enterobacter, Serratia, Proteus, Providencia, Yersinia, Pseudomonas, Acinetobacter, Moraxella and Pasteurella.

The medium grows the bacteria from a certain population which will normally be described in terms of CFU as above defined and will normally be referenced to the population in a certain volume of medium, i.e., CFU/ml. The beginning concentration can range as low as $1-2 \times 10^6$ CFU/ml but will normally be, and is preferably, at least $5 \times 10^6$ CFU/ml.

Starting with a lower initial population or concentration will not cause the medium to grow the bacteria to a significantly different final population or concentration than with a higher starting concentration but will affect the time it takes for the final concentration to be reached. Thus, if one is to control the incubation time the beginning concentration must be controlled. The final concentration to which the bacteria grow is referred to as the stationary phase.

As above discussed the time to reach a concentration equivalent to the McFarland standard varies according to the test procedure from 2 to 8 hours with most bacteria taking at least 5 to 6 hours to reach that concentration. With the growth limiting medium the bacteria preferably reach the final concentration or stationary phase within 5 hours. With the growth limiting medium if the bacteria reaches the stationary phase in 2 hours it will remain there even if the technician does not check the medium for 5 hours and no dilution will be required to obtain a concentration equivalent to the McFarland standard.

When the stationary phase or final concentration is reached the growth of the bacteria substantially subsides. This is due to there being an exhaustion of at least one nutrient critical to the continuous growth of the bacteria and not to the formation of toxic byproducts by the bacteria which stop growth and can cause the population to decrease substantially. With the standard media used prior to the growth limiting medium and described in the Kirby-Bauer procedure the population of the bacteria which will be reached in order for growth to subside would be determined by toxic byproducts of the bacteria. This population of bacteria is above the McFarland standard.

The final concentration or maximum stationary phase is obtained because of exhaustion of one or more nutrients. At that point the viable CFU/ml count levels off and remains substantially unchanged for at least about 18 hours. The bacteria remain viable for a period of time useful for carrying out the various tests to be performed thereon for example those described above. Normally the time period for such viability is at least 18 hours.

The final concentration which is desired to be reached with most bacteria will be between $6 \times 10^7$ to $3.0 \times 10^8$ CFU/ml. This is equivalent to the 0.5 McFarland standard. The medium can be modified to reach different desired concentration levels.

The medium will contain different types and amounts of ingredients depending upon the final concentration of bacteria desired and depending upon the type of bacteria being grown. In all cases a carbon and nitrogen source are present which provide carbon and nitrogen in a form useful by the bacteria for growth. Normally vitamins and minerals are also present. However, as noted, the amount of one or more of these ingredients is limited to cause the bacteria to reach a final predetermined concentration and substantially cease growing.

For the gram-negative bacteria a preferred medium comprises about 0.42 to about 0.70 milligrams of carbon per milliliter of medium. The carbon is in a form useful by the bacteria for growth. This form has been found to be that form in which carbon is present in peptone or a similar form. The preferred medium also comprises 0.09 to 0.15 milligrams of nitrogen per milliliter of medium in a form similar to the nitrogen present in peptone. The preferred medium has a pH from about 7 to 8. With proteose peptone the range for carbon is from about 0.16 to about 0.27 milligrams of carbon per milliliter of medium, the nitrogen is 0.035 to 0.056 milligrams of nitrogen per milliliter of medium and the carbon and nitrogen are as found in proteose peptone or a form similar thereto. A typical analysis of the peptone is set forth below

| Percent | Peptone | Proteose Peptone |
|---|---|---|
| Total Nitrogen | 16.16 | 14.37 |
| Primary Proteose N | 0.06 | 0.60 |
| Secondary Proteose N | 0.68 | 4.03 |
| Peptone N | 15.38 | 9.74 |
| Ammonia N | 0.04 | 0.00 |

| Percent | Peptone | Proteose Peptone |
| --- | --- | --- |
| Free Amino | 3.20 | 2.66 |
| Amide N | 0.49 | 0.94 |
| Mono-amino N | 9.42 | 7.61 |
| Di-amino N | 4.07 | 4.51 |
| Tryptophane | 0.29 | 0.51 |
| Tryosine | 0.98 | 2.51 |
| Crystine | 0.22 | 0.56 |
| Organic Sulfur | 0.33 | 0.60 |
| Inorganic Sulfur | 0.29 | 0.04 |
| Phosphorus | 0.22 | 0.47 |
| Chlorine | 0.27 | 3.95 |
| Sodium | 1.08 | 2.84 |
| Potassium | 0.22 | 0.70 |
| Calcium | 0.058 | 0.137 |
| Magnesium | 0.056 | 0.118 |
| Manganese | nil | 0.0002 |
| Iron | 0.0033 | 0.0056 |
| Ash | 3.53 | 9.61 |
| Ether Soluble Extract | 0.37 | 0.32 |
| Reaction, pH | 7.0 | 6.8 | pH 1% solution is distilled water after autoclaving 15 minutes at 121° C.

The preferred formulation contains the vitamins and minerals found in peptone or proteose peptone. Two specifically preferred formulatons which have been found to be useful in growing the gram-negative bacteria to a final concentration of from $6 \times 10^7$ to $3 \times 10^8$ CFU/ml in less than 5 hours comprises a mixture of 1000 ml of water containing 0.8 gram peptone or 0.3 gram proteose peptone, 0.03 gram dextrose, 2.5 gram dipotassium phosphate, 1.25 gram monopotassium phosphate and 5.0 grams sodium chloride. The phosphates are added as a buffer material to maintain the composition at pH of approximately 7.0. Buffering is necessary with certain of the bacteria. The aforesaid two formulations provide a medium upon which species from most of the genera of the gram-negative, aerobic, pathogenic bacteria can grow to the above described CFU/ml ranges within 5 hours if the initial concentration of bacteria is sufficient, i.e., at least about $5 \times 10^6$ CFU/ml.

As noted the preferred carbon and nitrogen sources are peptone and proteose peptone for the gram-negative bacteria. Neopeptone, tryptone and polypeptone can also be used but it has been found that these do not produce growth to the levels of the McFarland standard within the same time frame and with some of the bacteria within this group do not provide the appropriate nutrients to grow the bacteria to any significant degree. Therefore, these materials are useful for more limited numbers of bacteria. However, combination of such materials with peptone or proteose peptone can be used to provide a medium useful with a larger number of bacteria.

A preferred medium for use with the gram-positive bacteria comprises a solution of 1000 ml of water containing 0.2 grams peptone, 0.08 gram phytone, 0.03 gram dextrose, 5.0 grams sodium chloride, 0.25 gram dipotassium phosphate, 2.50 grams dibasic potassium hydrogen phosphate and 1.25 grams monobasic potassium hydrogen phosphate.

Applicants have found a device which utilizes the above described growth limiting medium and allows one to obtain from colonies of bacteria a certain predetermined amount of bacteria so that the growth limiting media is inoculated with a predetermined number of bacteria. This allows the time period for growth of the bacteria to be predetermined as well. In order for the requisite growth to occur within the preferred time of within 5 hours for the gram-negative bacteria, the beginning population must be at least about $5 \times 10^6$ CFU/ml.

Applicants have, therefore, discovered a device for growing bacteria from an initial population to a predetermined ending population between $6 \times 10^7$ and $3.0 \times 10^8$ CFU/ml at which the growth of said bacteria substantially subsides due to the lack of nutrient comprising (a) a vessel containing a supply of growth medium capable of growing said bacteria from said beginning population to said predetermined ending population, said vessel containing an opening, (b) means within said vessel for obtaining a predetermined quantity of bacteria from at least one growth colony of said bacteria external of said vessel and for inoculating said growth medium, and (c) removable means for covering said opening in said vessel to preserve the sterility of the inside of said vessel, for permitting said means for obtaining said bacteria to be removed to obtain said predetermined quantity of bacteria from said colony of said bacteria external of said vessel, which bacteria are used to inoculate said medium and for closing said vessel during the incubation of said inoculated medium; wherein said means for obtaining a predetermined quantity of bacteria comprises a rod attached at one end to said removable means, with a groove in the end of said rod opposite to that attached to said removable means, for picking up said bacteria by means of capillary action.

The device will be described in more detail with reference to the following drawings in which FIG. 1 is an exploded sectional view of the device of the present invention;

FIG. 2 is a prospective view of the device of the present invention with parts in section;

FIG. 3 is an exploded view of a portion of the wand of the device of the present invention;

FIG. 4 is the wand of FIG. 3 showing the inclusion therein of bacteria;

FIG. 5 is a sectional view of the device of the present invention just after inoculation of the growth medium with the bacteria;

FIG. 6 depicts a section of the device of the present invention as shown in FIG. 5 taken along line 6—6;

FIG. 7 is a section of the device of the present invention after inoculation and incubation to the maximum stationary phase or the predetermined growth stage; and FIG. 8 depicts a section of the device of FIG. 7 taken along line 8—8

FIG. 9 is an exploded view of a portion of another wand which may be substituted for the wand depicted in FIG. 3 in the device of the present invention.

The device of the present invention comprises a vessel or sleeve 1 which is made of a transparent deformable material such as polypropylene, polyamide, cellulose acetate butyrate or various polyesters. Contained within the sleeve 1 is glass ampoule 2 which contains within it the growth limiting medium 3 as above described. The glass ampoule as will be discussed later is frangible, i.e., it breaks when the deformable sleeve 1 is squeezed. In juxtaposition to the ampoule 2 of the device is wand 4 which contains groove 14 or tapered groove 5 which will be described in more detail with reference to FIGS. 3, 4 and 9. Wand 4 is used to pick the bacteria from the various colonies of bacteria and is made to ingest a predetermined amount of bacteria from the colonies into the groove 14 or tapered groove 5. Wand 4 is affixed to cap 6. Both cap 6 and wand 4 are made from plastic material such as polypropylene. Interior to cap 6 are two ridges 7 and 8 which allow for an aseptic seal between the cap 6 and sleeve 1. This prevents other microorganisms from entering the sleeve 1 prior to the time that the device is inoculated as well as during incubation. Also contained within cap 6 are three prongs 9, two of which are shown in FIG. 1. These prongs protect hole 10 in cap 6 from being blocked by broken glass from ampoule 2 (caused when the device is activated) during the time when deformable sleeve 1 is being deformed to express or exude the bacteria and medium 3 via hole 10. Hole 10 is covered with pressure sensitive adhesive tape 11 containing tab 12 during the time prior to use of the device and up until incubation of the device is complete. At that time tape 11 is removed exposing hole 10. This allows for the medium 3 and bacteria to be exuded or expressed from the sleeve 1.

FIG. 2 shows the device in its normal form prior to use except the pressure sensitive adhesive tape 11 is not present. As can be seen, wand 4 is adjacent to ampoule 2 and rims 7 and 8 are in juxtaposition to the upper portion of sleeve 1. In this case hole 10 is exposed to show it from a prospective view and pressure sensitive adhesive tape 11 is not shown. Prongs 9 are not visible in this view. Glass ampoule 2 is normally 35.6 millimeters by 6.3 millimeters in dimensions and contains approximately 0.6 milliliter of growth media. The sleeve 1 is normally 43.0 millimeters long and 8.6 millimeters in diameter.

An important feature of the device of the present invention is the wand 4 containing groove 14 or tapered groove 5. Groove 5 is shown in more detail in FIG. 3. These grooves are designed to provide a capillary action by which the bacteria are pushed into grooves 14 or 5. As the bacteria are pushed by means of pushing the wand 4 perpendicular to the surface of the colony so that the open end of either groove 14 or tapered groove 5 first contacts the colony, the bacteria begin to move up the groove and air is exuded from the opposite end of the groove. At a certain predetermined level no further bacteria can be pushed into the groove because bacteria which are continually forced into grooves 14 or 5 move out of the top of grooves 14 or 5. FIG. 4 shows schematically the bacteria 13 in the groove 5 at the normal filled groove level. Grooves 14 and 5 are designed to allow a certain population of bacteria to enter the grooves. This is normally equivalent to at least $5 \times 10^6$ bacteria per milliliter when the bacteria are placed in the medium of the device of the present invention. A groove about 0.43 millimeters deep, 0.25 millimeters wide at its largest end (assuming no taper) and 3.1 millimeters long will allow for the aforesaid pick-up. The groove can be modified to accomplish different desired populations of bacteria.

The use of the device will be described now with reference to FIGS. 5 through 8. FIG. 5 illustrates schematically with the device in section the device of the present invention just after inoculation of the device using wand 4. Cap 6 has been removed from the sleeve 1 and wand 4 via either tapered groove 5 or groove 14 has picked up bacteria from 4 to 5 colonies of bacteria a sufficient amount of bacteria to inoculate the device, normally at least $5 \times 10^6$ bacteria. Cap 6 has been replaced and the bacteria via wand 4 and grooves 5 or 14 were placed adjacent to the ampoule 2. As shown in FIG. 5 the ampoule 2 has been broken by deforming sleeve 1 and the bacteria 13 are now shown schematically in the growth limiting media 3. The device in this form will be incubated at approximately 35° C. for normally from 2 to 8 hours, with the preferred growth media for approximately 5 hours to obtain the predetermined preferred amount of bacteria. i.e., from $6 \times 10^7$ to $3 \times 10^8$ CFU/ml. FIG. 6 depicts in section the device of FIG. 5 at this beginning stage of incubation and shows the sleeve 1 containing broken ampoule 2, growth media 3 and bacteria 13.

After incubation the device is in the form shown in FIG. 7. In this case all of the device is just as it was before except as can be seen the population of bacteria 13 has increased significantly. FIG. 8 is a section of the device of FIG. 7 at this stage. In use after incubation the device of FIG. 7 shows that the tape 11 has been removed and that the device is ready now for exuding of the grown bacteria via hole 10. The device is merely held with hole 10 in a downward direction, sleeve 1 is squeezed and deformed and the bacteria 13 and media 3 are exuded via hole 10. Broken glass from ampoule 2 is precluded from plugging the hole via prongs 9.

Grooves 5 and 14 in the wand 4 can be changed to affectuate a different size inoculum of bacteria so that the population of bacteria picked up is greater than or less than that above described. Other configurations than a groove could be used in the present invention as long as there is an ability of the wand or pick-up device to pick on a repeatable basis a predetermined amount of bacteria. The device then in combination will allow the bacteria to grow from a certain predetermined level which is determined by the pick-up device to a final level which is determined by the growth limiting media in a certain period of time, which time period is determined by the beginning population, the growth limiting media formulation and type of bacteria. For use in a Kirby-Bauer test or MIC test it is preferred to have the device grow the bacteria within 5 hours to a concentration of from about $6 \times 10^7$ to $3 \times 10^8$ CFU/ml.

The device as shown contains the growth limiting media 3 in a glass ampoule 2. Other modifications can be made to affectuate the same results. For example, the device can merely be a threaded sleeve with a screw-on cap which has attached to it the wand. In this case the growth limiting medium is within the sleeve and is inoculated directly when the cap was removed. The bacteria are picked up with the wand and the cap screwed back on placing the wand in the medium. Other modifications will be apparent to one skilled in the art and are included within the claims.

The device depicted in FIG. 1 is made by molding and forming the various glass and plastic components. Approximately 0.6 milliliter of medium 3 is placed in glass ampoule 2 and the glass ampoule 2 is heat sealed. The ampoule 2 is steam sterilized for 10 minutes at 121° C. The sleeve 1, cap 6 and tape 11 are ethylene oxide, gas sterilized for 3 hours at 100° F. and then aerated for 8 hours. The sealed and sterilized glass ampoule 2 is asceptically added to the sleeve 1; the cap 6 is attached and the tap 11 is pressed into place.

In the following examples the following materials and bacteria are referenced. Their source is set forth below. In the examples growing device means a device as described above with the dimensions and prepared as described above.

Tryptone, an enzymatic hydrolysate of casein, Difco, Inc., Detroit, Michigan

Peptone, an enzymatic hydrolysate of casein, Difco, Inc., Detroit, Michigan

Dextrose, Difco, Inc., Detroit, Michigan

Polypeptone, an enzymatic hydrolysate of casein and animan tissue, Bioquest, Inc., Baltimore, Maryland Neopeptone, an enzymatic hydrolysate of protein, Difco, Inc., Detroit, Michigan Proteose peptone, an enzymatic hydrolysate of protein, Difco, Inc., Detroit, Michigan Salmonella typhimurium, American Type Culture Collection, (ATCC) No. 19028

Shigella Sonnei, (ATCC 25331)

Enterobacter cloacae (ATCC 23355) and St. Paul Ramsey Hospital, St. Paul, Minnesota

*Klebsiella pneumoniae*, (ATCC 23357) and St. Paul Ramsey Hospital, St. Paul, Minnesota

*Proteus vulgaris* (ATCC 6380)

*Proteus mirabilis*, St. John's Hospital, St. Paul, Minn. and St. Paul Ramsey Hospital, St. Paul, Minn.

*Serratia marcescens* (ATCC 8100) and St. Paul Ramsey Hospital, St. Paul, Minn.

Providencia species, University of Minnesota, Minneapolis, Minn.

Citrobacter species, University of Minnesota, Minneapolis, Minn.

Edwardsiella, University of Minnesota, Minneapolis, Minn.

Arizona, University of Minnesota, Minneapolis, Minn.

Yersinia, University of Minnesota, Minneapolis, Minnesota

*Pseudomonas aeruginosa* (ATCC 27853) St. Paul Ramsey Hospital, St. Paul, Minn.

*Escherichia coli* (ATCC 25922) and St. Paul Ramsey Hospital, St. Paul, Minn.

*Acinetobacter calcoaceticus*, St. Paul Ramsey Hospital, St. Paul, Minn.

*Proteus morganii*, St. Paul Ramsey Hospital, St. Paul, Minn.

*Enterobacter aerogenes*, St. Paul Ramsey Hospital, St. Paul, Minn.

Pasteurella (species), St. Paul Ramsey Hospital, St. Paul, Minn.

CDC Group II F, St. Paul Ramsey Hospital, St. Paul, Minn.

Moraxella, St. Paul Ramsey Hospital, St. Paul, Minn.

*Citrobacter freundii*, St. Paul Ramsey Hospital, St. Paul, Minn.

EXAMPLE 1

Devices having the specifications described above were inoculated with various bacteria using the tapered grooves of the wand of the device. An initial concentration of bacteria was noted. The growth limiting media included within the ampoule of each device contains the following:

0.8 gram Peptone
0.03 gram Dextrose
2.5 grams Dipotassium phosphate
1.25 grams Monopotassium phosphate
5.0 grams Sodium chloride Solutions of media containing 0.2 gram peptone and 1.6 grams peptone were also prepared.

Four other growth limiting media were used which include proteose peptone, tryptone, neopeptone and polypeptone. These were substituted for the peptone of the above formulation. The resulting initial concentrations were determined and are as follows in CFU/ml.

The results given are the mean of 15 samples, i.e., 5 samples of each of the 3 formulations of each medium.

| | Peptone | Proteose Peptone | Tryptone | Neo-peptone | Poly peptone |
|---|---|---|---|---|---|
| *Escherichia coli* | $1.8 \times 10^7$ | $2.1 \times 10^7$ | $3.6 \times 10^7$ | — | $1.4 \times 10^7$ |
| *Shigella* | $3.0 \times 10^7$ | $6.0 \times 10^7$ | — | — | $2.3 \times 10^7$ |
| *Klebsiella* | $2.7 \times 10^7$ | $3.7 \times 10^7$ | $5.3 \times 10^7$ | — | $3.3 \times 10^7$ |
| *Enterobacter* | $4.5 \times 10^7$ | $4.0 \times 10^7$ | $8.8 \times 10^7$ | — | — |
| *Providencia* | $7.5 \times 10^7$ | $7.0 \times 10^7$ | $3.6 \times 10^7$ | — | — |
| *Proteus Mirabilis* | $4.8 \times 10^7$ | $5.6 \times 10^7$ | $2.9 \times 10^7$ | — | — |
| *Salmonella* | $2.8 \times 10^7$ | $4.0 \times 10^7$ | $1.5 \times 10^7$ | $2.9 \times 10^7$ | $1.8 \times 10^7$ |
| *Pseudomonas* | $0.8 \times 10^7$ | $1.9 \times 10^7$ | $3.1 \times 10^7$ | — | $6.4 \times 10^7$ |
| *Citrobacter* | $4.5 \times 10^7$ | $4.5 \times 10^7$ | $2.9 \times 10^7$ | $8.0 \times 10^7$ | $23.9 \times 10^7$ |
| *Arizona* | $1.5 \times 10^7$ | $2.4 \times 10^7$ | — | $3.0 \times 10^7$ | — |
| *Edwardsiella* | $2.4 \times 10^7$ | — | — | — | — |
| *Yersinia* | $3.3 \times 10^7$ | $5.1 \times 10^7$ | $2.8 \times 10^7$ | $5.7 \times 10^7$ | $4.4 \times 10^7$ |
| *Serratia* | $1.3 \times 10^7$ | $7.5 \times 10^7$ | $3.9 \times 10^7$ | $3.9 \times 10^7$ | $4.4 \times 10^7$ |
| *Proteus vulgaris* | $1.2 \times 10^7$ | — | — | $2.7 \times 10^7$ | $2.6 \times 10^7$ |

Species of bacteria are as above listed.
Where there are blanks the inoculum was in error.

EXAMPLE 2

The following materials were dissolved in 1000 milliliters of deionized water and steam sterilized at 121° C. for 15 minutes:

0.8 gram Peptone
0.03 gram Dextrose
2.5 grams Dipotassium phosphate
1.25 grams Monopotassium phosphate
5.0 grams Sodium chloride Solutions of media containing 0.2 gram peptone and 1.6 grams peptone were also prepared. Growing devices were then prepared using each of the media. Utilizing the wand 4 of the growing device, bacteria were picked up from 4 to 5, 18 to 24 hour old bacterial colonies of the various bacteria set forth in the table below. Five growing devices were used for each bacteria to obtain a mean of 5 samples for each bacteria. Fourteen different bacteria were tested; thus, there were 70 growing devices utilized in the test for each of the 3 media. Each growing device was vortexed, i.e., mixed for 10 seconds and incubated at 35° C. Viable bacteria counts were performed at 0, 4, 5 and 6 hours. The results are set forth in the table below:

TABLE 2

| | | Count ($\times 10^7$ CFU/ml) | | |
|---|---|---|---|---|
| Bacteria | Time | 0.2g | 0.8g | 1.6g |
| *Escherichia coli* | 0 hours | 1.6 | 1.44 | 2.4 |
| | 4 hours | 0.4 | 5.2 | 1.6 |
| | 5 hours | 3.7 | 10.2 | 14.8 |
| | 6 hours | 1.3 | 7.6 | 15.4 |
| *Shigella sonnei* | 0 hours | 4.2 | 3.62 | 1.2 |
| | 4 hours | 5.7 | 14.4 | 15.8 |
| | 5 hours | 8.1 | 17.0 | 19.8 |
| | 6 hours | 6.0 | 12.2 | 21.0 |
| *Klebsiella pneumoniae* | 0 hours | 2.6 | 2.86 | 2.6 |
| | 4 hours | 5.3 | 13.4 | 11.6 |
| | 5 hours | 4.9 | 13.6 | 13.6 |
| | 6 hours | 4.9 | 12.0 | 16.0 |
| *Enterobacter cloacae* | 0 hours | 5.3 | 4.4 | 3.9 |
| | 4 hours | 9.4 | 17.0 | 17.4 |
| | 5 hours | 9.2 | 19.0 | 26.0 |

TABLE 2-continued

| Bacteria | Time | Count ($\times 10^7$ CFU/ml) 0.2g | 0.8g | 1.6g |
|---|---|---|---|---|
| | 6 hours | 9.4 | 19.6 | 38.6 |
| Providencia species | 0 hours | 7.3 | 6.14 | 9.1 |
| | 4 hours | 11.6 | 22.2 | 30.2 |
| | 5 hours | 13.2 | 27.4 | 38.6 |
| | 6 hours | 13.2 | 22.8 | 39.8 |
| Proteus mirabilis | 0 hours | 4.2 | 4.66 | 5.4 |
| | 4 hours | 8.9 | 21.4 | 21.4 |
| | 5 hours | 8.6 | 19.8 | 33.2 |
| | 6 hours | 9.7 | 24.0 | 37.2 |
| Salmonella typhimurium | 0 hours | 2.4 | 2.32 | 3.8 |
| | 4 hours | 6.6 | 16.4 | 27.8 |
| | 5 hours | 7.1 | 16.4 | 31.0 |
| | 6 hours | 6.8 | 19.0 | 33.2 |
| Pseudomonas aeruginosa | 0 hours | 1.0 | 0.7 | 0.8 |
| | 4 hours | 5.6 | 14.6 | 11.4 |
| | 5 hours | 3.6 | 16.6 | 18.6 |
| | 6 hours | 5.3 | 26.4 | 29.2 |
| Citrobacter species | 0 hours | 3.8 | 31.0 | 6.6 |
| | 4 hours | 9.2 | 20.8 | 21.0 |
| | 5 hours | 9.3 | 20.8 | 30.6 |
| | 6 hours | 12.6 | 31.4 | 32.6 |
| Arizona | 0 hours | 1.1 | 1.46 | 2.0 |
| | 4 hours | 41. | 15.2 | 16.0 |
| | 5 hours | 4.9 | 16.0 | 21.8 |
| | 6 hours | 4.9 | 17.6 | 26.2 |
| Edwardsiella | 0 hours | 2.2 | 2.98 | 1.9 |
| | 4 hours | 2.3 | 6.04 | 8.3 |
| | 5 hours | 2.5 | 6.02 | 8.8 |
| | 6 hours | 2.4 | 5.9 | 10.5 |
| Yersinia | 0 hours | 3.3 | 3.02 | 3.7 |
| | 4 hours | 5.0 | 9.9 | 16.0 |
| | 5 hours | 5.4 | 11.5 | 19.2 |
| | 6 hours | 6.7 | 13.0 | 21.2 |
| Serrati marcescens | 0 hours | 1.1 | 1.62 | 1.1 |
| | 4 hours | 5.2 | 10.0 | 14.0 |
| | 5 hours | 6.3 | 16.8 | 17.8 |
| | 6 hours | 6.8 | 26.3 | 23.4 |
| Proteus vulgaris | 0 hours | 1.7 | 1.36 | 0.5 |
| | 4 hours | 6.5 | 19.36 | 19.2 |
| | 5 hours | 6.3 | 23.2 | 31.4 |
| | 6 hours | 7.3 | 22.0 | 34.5 |

EXAMPLE 3

Example 2 was repeated except that polypeptone was substituted for peptone. The result are set forth in the table below:

TABLE 3

| Bacteria | Time | Count ($\times 10^7$ CFU/ml) 0.2g | 0.8g | 1.6g |
|---|---|---|---|---|
| Escherichia coli | 0 hours | 1.4 | 0.8 | 1.1 |
| | 4 hours | 7.8 | 9.8 | 6.8 |
| | 5 hours | 6.0 | 5.5 | 5.5 |
| | 6 hours | 6.7 | 7.9 | 7.9 |
| Shigella sonnei | 0 hours | 1.7 | 1.68 | 2.8 |
| | 4 hours | 7.1 | 9.98 | 10.6 |
| | 5 hours | 6.4 | 9.88 | 11.4 |
| | 6 hours | 8.0 | 11.4 | 11.0 |
| Klebsiella pneumoniae | 0 hours | 3.0 | 3.64 | 3.3 |
| | 4 hours | 6.9 | 4.78 | 7.1 |
| | 5 hours | 7.0 | 7.3 | 8.0 |
| | 6 hours | 7.8 | 12.6 | 9.5 |
| Enterobacter cloacae | 0 hours | 4.2 | 3.2 | 1.8 |
| | 4 hours | 16.2 | 19.0 | 8.1 |
| | 5 hours | 15.8 | 12.8 | 13.2 |
| | 6 hours | 11.6 | 13.6 | 16.8 |
| Providencia species (inoculum error) | 0 hours | — | — | — |
| | 4 hours | — | — | — |
| | 5 hours | — | — | — |
| | 6 hours | — | — | — |
| Proteus mirabilis | 0 hours | 0.46 | 0.46 | 0.34 |
| | 4 hours | 2.7 | 3.86 | 3.6 |
| | 5 hours | 7.6 | 14.6 | 13.0 |
| | 6 hours | 7.5 | 10.6 | 11.4 |
| Salmonella typhimurium | 0 hours | 1.3 | 1.4 | 0.91 |

TABLE 3-continued

| Bacteria | Time | Count ($\times 10^7$ CFU/ml) 0.2g | 0.8g | 1.6g |
|---|---|---|---|---|
| | 4 hours | 6.8 | 6.9 | 7.4 |
| | 5 hours | 10.0 | 11.8 | 10.7 |
| | 6 hours | 9.0 | 14.1 | 11.0 |
| Pseudomonas aeruginosa | 0 hours | 5.8 | 7.7 | 5.6 |
| | 4 hours | 8.0 | 8.3 | 11.0 |
| | 5 hours | — | 22.2 | 24.8 |
| | 6 hours | 7.5 | 20.3 | 23.6 |
| Citrobacter species | 0 hours | 15.4 | 21.6 | 34.2 |
| | 4 hours | 16.6 | 22.4 | 22.2 |
| | 5 hours | 14.8 | 31.4 | 25.6 |
| | 6 hours | 15.2 | 27.2 | 30.4 |
| Arizona | 0 hours | 3.7 | 4.0 | 3.2 |
| | 4 hours | 5.3 | 6.6 | 5.6 |
| | 5 hours | 6.6 | 13.2 | 12.5 |
| | 6 hours | 7.0 | 20.8 | 17.2 |
| Edwardsiella | 0 hours | | No growth | |
| | 4 hours | | No growth | |
| | 5 hours | | No growth | |
| | 6 hours | | No growth | |
| Yersinia | 0 hours | 4.4 | 2.85 | 5.7 |
| | 4 hours | 4.4 | 5.0 | 10.7 |
| | 5 hours | 8.0 | 9.73 | 17.2 |
| | 6 hours | 8.6 | 11.0 | 18.6 |
| Serratia marcescens | 0 hours | 4.4 | 4.6 | 4.1 |
| | 4 hours | 13.6 | 11.1 | 8.8 |
| | 5 hours | 15.2 | 14.4 | 10.1 |
| | 6 hours | 15.4 | 15.0 | 13.6 |
| Proteus vulgaris | 0 hours | 4.5 | 2.64 | 1.4 |
| | 4 hours | 6.9 | 7.92 | 4.2 |
| | 5 hours | 15.5 | 15.4 | 11.3 |
| | 6 hours | 16.5 | 18.0 | 15.3 |

EXAMPLE 4

Example 2 was repeated except that neopeptone was substituted for the peptone. The results are set forth in the table below:

TABLE 4

| Bacteria | Time | Count ($\times 10^7$ CFU/ml) 0.2g | 0.8g | 1.6g |
|---|---|---|---|---|
| Escherichia coli | 0 hours | 0.84 | 1.0 | 0.55 |
| | 4 hours | 0.54 | 0.6 | 0.38 |
| | 5 hours | 1.8 | 1.96 | 1.1 |
| | 6 hours | 1.3 | 4.0 | 3.0 |
| Shigella sonnei | 0 hours | 1.8 | 0.8 | 0.79 |
| | 4 hours | 3.3 | 2.3 | 1.0 |
| | 5 hours | 4.6 | 6.2 | 4.2 |
| | 6 hours | 6.3 | 6.1 | 4.0 |
| Klebsiella pneumoniae | 0 hours | 0.2 | 0.13 | 0.1 |
| | 4 hours | 3.7 | 2.5 | 4.0 |
| | 5 hours | 7.2 | 2.5 | 8.0 |
| | 6 hours | 5.3 | 5.8 | 8.2 |
| Enterobacter cloacae | 0 hours | | No growth | |
| | 4 hours | | No growth | |
| | 5 hours | | No growth | |
| | 6 hours | | No growth | |
| Providencia species | 0 hours | 0.4 | — | 0.2 |
| | 4 hours | 0.7 | — | 0.6 |
| | 5 hours | 1.4 | — | 0.7 |
| | 6 hours | 1.9 | — | 1.8 |
| Proteus mirabilis | 0 hours | 2.0 | 1.0 | 4.2 |
| | 4 hours | 6.3 | 8.5 | 6.8 |
| | 5 hours | 10.0 | 17.6 | 16.0 |
| | 6 hours | 10.5 | 21.8 | 22.2 |
| Salmonella typhimurium | 0 hours | 3.3 | 2.48 | 2.6 |
| | 4 hours | 7.2 | 8.92 | 8.0 |
| | 5 hours | 13.2 | 17.2 | 19.0 |
| | 6 hours | 12.6 | 16.6 | 18.0 |
| Pseudomonas aeruginosa | 0 hours | 0.2 | 0.16 | 0.24 |
| | 4 hours | 1.8 | 5.9 | 4.9 |
| | 5 hours | 5.3 | 9.5 | 9.6 |
| | 6 hours | 7.2 | 18.0 | 16.0 |
| Citrobacter species | 0 hours | 5.4 | 7.62 | 13.0 |
| | 4 hours | 7.4 | 7.44 | — |
| | 5 hours | 12.2 | 24.6 | 27.2 |

TABLE 4-continued

| Bacteria | Time | Count (× 10⁷ CFU/ml) | | |
|---|---|---|---|---|
| | | 0.2g | 0.8g | 1.6g |
| | 6 hours | 15.6 | 30.2 | 31.4 |
| Arizona | 0 hours | 3.4 | 3.0 | 2.6 |
| | 4 hours | 6.3 | 6.6 | 7.6 |
| | 5 hours | 7.9 | 13.0 | 11.8 |
| | 6 hours | 9.8 | 16.4 | 17.4 |
| Yersinia | 0 hours | 4.9 | 6.24 | 6.0 |
| | 4 hours | 6.0 | 10.7 | 10.8 |
| | 5 hours | 9.7 | 15.5 | 16.0 |
| | 6 hours | 10.4 | 20.6 | 21.0 |
| Edwardsiella | 0 hours | | No data | |
| | 4 hours | | No data | |
| | 5 hours | | No data | |
| | 6 hours | | No data | |
| Serratia marcescens | 0 hours | 3.5 | 3.16 | 5.1 |
| | 4 hours | 8.7 | 10.1 | 9.8 |
| | 5 hours | 11.3 | 11.6 | 12.3 |
| | 6 hours | 9.7 | 12.7 | 12.8 |
| Proteus vulgaris | 0 hours | 2.4 | 3.56 | 2.0 |
| | 4 hours | 5.5 | 12.5 | 8.1 |
| | 5 hours | 8.6 | 23.8 | 16.4 |
| | 6 hours | 10.7 | 28.4 | 23.2 |

EXAMPLE 5

Example 2 was repeated except that tryptone was substituted for peptone. The results are set forth in the table below:

TABLE 5

| Bacteria | Time | Count (× 10⁷ CFU/ml) | | |
|---|---|---|---|---|
| | | 0.2g | 0.8g | 1.6g |
| Escherichia coli | 0 hours | 3.5 | 3.9 | 2.1 |
| | 4 hours | 12.2 | 17.8 | 13.5 |
| | 5 hours | 13.2 | 22.8 | 18.4 |
| | 6 hours | 13.0 | 25.2 | 23.2 |
| Shigella sonnei | 0 hours | 1.0 | 0.4 | 0.33 |
| | 4 hours | 6.3 | 11.0 | 10.0 |
| | 5 hours | 7.1 | 16.0 | 16.0 |
| | 6 hours | 8.2 | 21.3 | 22.3 |
| Klebsiella pneumoniae | 0 hours | 5.9 | 5.32 | 4.7 |
| | 4 hours | 13.2 | 14.2 | 16.2 |
| | 5 hours | 14.0 | 15.8 | 15.4 |
| | 6 hours | 13.0 | 19.6 | 19.4 |
| Enterobacter cloacae | 0 hours | 8.7 | 7.08 | 10.6 |
| | 4 hours | 15.4 | 29.0 | 24.2 |
| | 5 hours | 15.2 | 34.2 | 33.4 |
| | 6 hours | 17.4 | 40.6 | 39.4 |
| Providencia species | 0 hours | 3.2 | 3.62 | 3.9 |
| | 4 hours | 8.2 | 16.4 | 17.0 |
| | 5 hours | 8.2 | 22.4 | 22.2 |
| | 6 hours | 5.8 | 24.6 | 27.4 |
| Proteus mirabilis | 0 hours | 3.3 | 2.08 | 3.3 |
| | 4 hours | 11.8 | 16.2 | 19.8 |
| | 5 hours | 11.1 | 21.6 | 19.0 |
| | 6 hours | 13.0 | 26.2 | 24.0 |
| Salmonella typimurium | 0 hours | 1.1 | 1.56 | 1.0 |
| | 4 hours | 7.5 | 15.6 | 11.6 |
| | 5 hours | 8.0 | 21.4 | 13.8 |
| | 6 hours | 10.6 | 27.6 | 19.2 |
| Pseudomonas aeruginosa | 0 hours | 3.4 | 2.52 | 2.9 |
| | 4 hours | 10.0 | 11.0 | 11.6 |
| | 5 hours | 11.0 | 10.4 | 13.0 |
| | 6 hours | | | |
| Citrobacter species | 0 hours | 3.3 | 2.66 | 2.4 |
| | 4 hours | 16.6 | 15.8 | 17.2 |
| | 5 hours | 16.8 | 25.4 | 20.4 |
| | 6 hours | 17.0 | 34.4 | 27.7 |
| Arizona | 0 hours | 1.4 | 1.0 | 0.66 |
| | 4 hours | 5.5 | 6.2 | 6.3 |
| | 5 hours | 5.7 | 12.0 | 10.2 |
| | 6 hours | 6.4 | 17.3 | 14.2 |
| Edwardsiella | 0 hours | 0.78 | 0.85 | 1.6 |
| | 4 hours | 2.3 | 1.9 | 3.4 |
| | 5 hours | 3.1 | 2.3 | 3.9 |
| | 6 hours | 2.9 | 2.8 | 4.8 |
| Yersinia | 0 hours | 2.0 | 1.58 | 2.7 |

TABLE 5-continued

| Bacteria | Time | Count (× 10⁷ CFU/ml) | | |
|---|---|---|---|---|
| | | 0.2g | 0.8g | 1.6g |
| | 4 hours | 5.1 | 5.8 | 10.0 |
| | 5 hours | 6.1 | 8.42 | 13.6 |
| | 6 hours | 7.1 | 12.8 | 18.3 |
| Serratia marcescens | 0 hours | 3.2 | 4.98 | 3.0 |
| | 4 hours | 16.6 | 20.8 | 15.6 |
| | 5 hours | 19.2 | 25.4 | 21.4 |
| | 6 hours | 23.2 | 29.8 | 25.8 |
| Proteus vulgaris | 0 hours | 1.46 | 1.1 | 1.0 |
| | 4 hours | 8.0 | 16.2 | 13.3 |
| | 5 hours | 10.0 | 16.5 | 18.0 |
| | 6 hours | 10.0 | 25.7 | 22.3 |

EXAMPLE 6

Example 2 was repeated except that proteose peptone was substituted for the peptone. The result are set forth in the table below:

TABLE 6

| Bacteria | Time | Count (× 10⁷ CFU/ml) | | |
|---|---|---|---|---|
| | | 0.2g | 0.8g | 1.6g |
| Escherichia coli | 0 hours | 2.2 | 1.78 | 1.9 |
| | 4 hours | 10.0 | 15.4 | 14.5 |
| | 5 hours | 7.4 | 22.0 | 22.0 |
| | 6 hours | 7.6 | 20.4 | 29.0 |
| Shigella sonnei | 0 hours | 6.9 | 6.38 | 4.6 |
| | 4 hours | 14.0 | 23.2 | 20.6 |
| | 5 hours | 13.4 | 20.8 | 28.8 |
| | 6 hours | 13.8 | 25.4 | 33.4 |
| Klebsiella pneumoniae | 0 hours | 4.1 | 3.52 | 3.5 |
| | 4 hours | 12.6 | 15.2 | 15.4 |
| | 5 hours | 12.8 | 26.0 | 23.4 |
| | 6 hours | 13.4 | 21.2 | 17.8 |
| Enterobacter cloacae | 0 hours | 4.2 | 0.8 | 4.3 |
| | 4 hours | 12.2 | 24.2 | 17.6 |
| | 5 hours | 13.0 | 28.3 | 27.0 |
| | 6 hours | — | 27.0 | 35.2 |
| Providencia species | 0 hours | 6.4 | 6.8 | 7.7 |
| | 4 hours | 19.2 | 33.2 | 32.0 |
| | 5 hours | 22.8 | 44.8 | 41.8 |
| | 6 hours | 24.6 | 49.6 | 44.6 |
| Proteus mirabilis | 0 hours | 5.6 | 5.98 | 5.3 |
| | 4 hours | 18.8 | 38.2 | 32.4 |
| | 5 hours | 18.8 | 38.2 | 38.0 |
| | 6 hours | 18.4 | 39.6 | 48.6 |
| Salmonella typhimurium | 0 hours | 3.0 | 3.86 | 5.0 |
| | 4 hours | 15.0 | 28.0 | 25.2 |
| | 5 hours | 15.0 | 34.2 | 30.6 |
| | 6 hours | 17.8 | 35.2 | 38.4 |
| Pseudomonas aeruginosa | 0 hours | 1.8 | 1.78 | 2.2 |
| | 4 hours | 5.4 | 7.98 | 11.3 |
| | 5 hours | 9.3 | 14.2 | 21.6 |
| | 6 hours | 8.7 | 15.8 | 19.0 |
| Citrobacter species | 0 hours | 4.4 | 3.82 | 5.2 |
| | 4 hours | 15.8 | 23.2 | 26.8 |
| | 5 hours | 16.6 | 27.6 | 28.2 |
| | 6 hours | 16.0 | 32.2 | 34.8 |
| Arizona | 0 hours | 2.5 | 1.92 | 2.7 |
| | 4 hours | 10.8 | 14.2 | 15.0 |
| | 5 hours | 11.2 | 22.4 | 17.8 |
| | 6 hours | 11.6 | 25.6 | 24.0 |
| Edwardsiella | 0 hours | 1.6 | 1.3 | 1.3 |
| | 4 hours | 3.6 | 5.9 | 10.3 |
| | 5 hours | 3.4 | 8.3 | 12.8 |
| | 6 hours | 3.9 | 10.0 | 15.8 |
| Yersinia | 0 hours | 6.4 | 3.0 | 5.9 |
| | 4 hours | 11.4 | 12.2 | 13.2 |
| | 5 hours | 13.4 | 18.0 | 19.6 |
| | 6 hours | 13.4 | 22.4 | 26.4 |
| Serratia marcescens | 0 hours | 9.9 | 6.14 | 6.5 |
| | 4 hours | 28.0 | 26.2 | 25.8 |
| | 5 hours | 27.6 | 30.2 | 27.6 |
| | 6 hours | 33.8 | 37.8 | 35.8 |
| Proteus vulgaris | 0 hours | 5.2 | 7.6 | 7.4 |
| | 4 hours | 12.6 | 19.6 | 18.4 |
| | 5 hours | 11.2 | 29.4 | 27.2 |

TABLE 6-continued

| Bacteria | Time | Count ($\times 10^7$ CFU/ml) | | |
|---|---|---|---|---|
| | | 0.2g | 0.8g | 1.6g |
| | 6 hours | 13.6 | 33.2 | 33.6 |

EXAMPLE 7

Devices having the specifications described were inoculated with gram-negative bacteria using the groove 14 of the wand of the device. An initial concentration of bacteria was noted. The growth limiting media included within the ampoule of each device contains the following:

0.8 gm/liter Peptone (Difco, Inc., (Detroit, MI)
0.03 gm/liter Dextrose (Difco Inc., Detroit, MI)
5.00 gm/liter Sodium Chloride (Mallinkrodt, Inc.), USP or better.
2.50 gm/liter Dibasic Potassium Hydrogen Phosphate (Mallinkrodt, Inc.,), purified or better.
1.25 gm/liter Monobasic Potassium Hydrogen Phosphate (Mallinkrodt, Inc.), purified or better.
0.10 gm/liter (polyoxyethylene (20) sorbitan monooleate)

Processed USP purity water

Specifically, 1 to 2 isolated colonies were touched with the wand from the growing device and the wand was used to inoculate the growing medium in the growing device. The units were incubated at 35° C. in an incubator for 7 hours. 10 ul aliquots were withdrawn at 0 time and periodically thereafter to determine the growth curve. The results were similar to those found in Table 2 (0.8 g), of Example 2.

EXAMPLE 8

Devices having the specifications described were inoculated with gram-positive bacteria using the groove 14 of the wand of the device. An initial concentration of bacteria was noted. The growth limiting media included within the ampoule of each device contains the following:

0.08 gm/liter Phytone (Bioquest Inc., Cockeysville, MD)
0.1 gm/liter Yeast Extract (Difco Inc., Detroit, MI)
0.2 gm/liter Peptone (Difco Inc., Detroit, MI)
0.25 gm/liter Dextrose (Difco Inc., Detroit, MI)
0.75 gn/liter Agar (Difco Inc., Detroit, MI) Bacto
5.00 gm/liter Sodium Chloride (Mallinkrodt, Inc.) USP or better
2.50 gm/liter Dibasic Potassium Hydrogen (Mallinkrodt, Inc.) Purified or better)
1.25 gm/liter Monobasic Potassium Hydrogen Phosphate (Mallinkrodt, Inc.), purified or better
0.20 gm/liter (polyoxyethylene (20) sorbitan monooleate) Processed USP Purity Water Specifically, 1 to 2 isolated colonies were touched with the wand device and the wand was used to inoculate the growing medium in the growing device. The units were incubated at 35° C. in an incubator for 7 hours. 10 ul aliquots were withdrawn at 0 time and periodically thereafter to determine the growth curve. The results were similar to those found in Table 2 (0.8 g), of Example 2.

EXAMPLE 9

In order to compare the medium of the present invention with the results obtained utilizing a standard broth growth technique, i.e., tryptic soy broth prior to placing the bacteria onto discs for use in the Kirby-Bauer procedure, 100 growing devices were prepared which contained the same medium as set forth in Example 2. One hundred clinical isolates of bacteria that were received from patients were run using both the growing device and the standard growing technique of the standard set forth for the Kirby-Bauer test. The bacteria tested included:

Escherichia coli
Klebsiella pneumoniae
Pseudomonas aeruginosa
Acinetobacter calocoaceticus
Proteus mirabilis
Proteus morganii
Enterobacter aerogenes
Enterobacter cloacae
Serratia marcescens
Pasteurella (species)
CDC Group II F
Moraxella
Citrobacter freundii Specifically, 4 to 5 isolated colonies were touched with the wand from the growing device and the wand was used to inoculate the growing medium in the growing device. The units were incubated at 35° C. in a 3M brand incubator Model 107 for 4 hours. The top tape seal was removed from the cap of the growing unit and 6 to 8 drops of bacterial suspension were dispensed onto a cotton swab. The swab was streaked in three directions over a Mueller-Hinton agar plate and the Kirby-Bauer test was completed according to the National Clinical Committee for Laboratory Standards (NCCLS) Antibiotics Susceptibility Standard set forth above. A comparison was made between the results obtained in respect to the susceptibility of the organism tested in using the growth media of the present invention versus the standard technique for growing bacteria. The results were comparable.

What we claim is:

1. A wand for picking up a predetermined quantity of bacteria from the surface of at least one growth colony of said bacteria consisting essentially of a rod-like member having a top end, and a lower colony-contacting tip, said lower tip having at least one groove in the lowermost end of said tip into which said bacteria are ingested, said groove being capable of ingesting said predetermined quantity of bacteria by capillary action.

2. The wand of claim 1 wherein at least one of said grooves is a tapered groove.

3. A method of picking-up a predetermined quantity of bacteria from the surface of a growth colony of said bacteria, comprising contacting the tip of a rod-like member having a top end, and a lower colony-contacting tip, said lower tip having at least one groove in the lowermost end of said tip, with said surface whereby said predetermined quantity of bacteria is ingested by said groove, said groove being capable of ingesting said predetermined quantity of bacteria by capillary action.

4. The method of claim 3 wherein said bacteria are ingested by said groove by capillary action.

5. A method of inoculating a vessel containing a liquid medium in one compartment thereof with a predetermined quantity of bacteria comprising:

picking-up a predetermined quantity of bacteria from the surface of a growth colony of said bacteria by contacting the tip of a rod-like member having a top end, and a lower colony-contacting tip, said lower tip having at least one groove in the lowermost end of said tip, with said surface whereby said predetermined quantity of bacteria is ingested by said groove; said groove being capable of ingesting said predetermined quantity of bacteria by capillary action;

placing said bacteria, via said rod-like member, adjacent said medium in said vessel; and causing said bacteria and said medium to come into contact with each other.

6. The method of claim 5 wherein said predetermined quantity of bacteria picked up is equivalent to at least $5 \times 10^6$ bacteria per milliliter when said bacteria are in contact with said medium.

7. A wand for picking-up a predetermined quantity of bacteria from the surface of at least one growth colony of said bacteria comprising a rod-like member having a top end, and a lower colony-contacting tip, said lower tip having at least one groove in the lowermost end of said tip into which said bacteria are ingested by capillary action, and said top end including means for releasably engaging and covering an opening in a vessel, when said wand is placed therein.

* * * * *